(12) United States Patent
Krouglicof et al.

(10) Patent No.: US 6,315,560 B1
(45) Date of Patent: Nov. 13, 2001

(54) HIGH-SPEED DENTAL DRILL

(75) Inventors: Nicholas Krouglicof, Montreal-West; Roland Maranzana, Montreal; Sylvain Lampron, Boucherville, all of (CA)

(73) Assignee: Ecole de technologie supérieure, Montréal ( * ) Notice: Subject to any disclaimer, the term of this patent is extended or adjusted under 35 U.S.C. 154(b) by 0 days.

(21) Appl. No.: 09/399,031

(22) Filed: Sep. 21, 1999

(51) Int. Cl.$^7$ ................................. A61C 1/05; A61C 1/08
(52) U.S. Cl. ............................................ 433/132; 433/126
(58) Field of Search ..................................... 433/126, 132, 433/114

(56) References Cited

U.S. PATENT DOCUMENTS

| | | | |
|---|---|---|---|
| 5,772,436 | * | 6/1998 | Matsui et al. ........................ 433/126 |
| 5,797,743 | * | 8/1998 | Bialey ................................. 433/126 |
| 5,902,108 | * | 5/1999 | Nakayama et al. .................. 433/132 |
| 5,938,441 | * | 8/1999 | Brenner ............................... 433/132 |

* cited by examiner

Primary Examiner—Nicholas D. Lucchesi
(74) Attorney, Agent, or Firm—Swabey Ogilvy Renault; Guy J. Houle

(57) ABSTRACT

A high-speed dental drill is comprised of a hand piece having a drill head at an end thereof. A turbine assembly is supported in a turbine chamber inside the drill head. The turbine assembly has a chuck which is rotatably secured between bearings. An impeller is secured about the chuck and aligned with an air inlet port in a sidewall of the turbine chamber. An exhaust port is provided in the sidewall to exhaust air. An air conduit is provided in the handpiece to direct air pressure to the air inlet port to drive the turbine and rotate the chuck. The chuck has a work bit engaging free end which is exteriorly accessible. An insert is secured to the drill head and provides access to the turbine chamber. The insert has a smooth conical tapered circumferential external sidewall for frictional engagement by a mating conical bore of a key for the removal and connection of the insert. The exhaust port has a non-circular cross-section in which the aspect ratio of the exhaust port is not equal to one. The handpiece, the drill head and the insert are all radially symmetric to facilitate cleaning and sterilization as well as manufacturing.

10 Claims, 4 Drawing Sheets

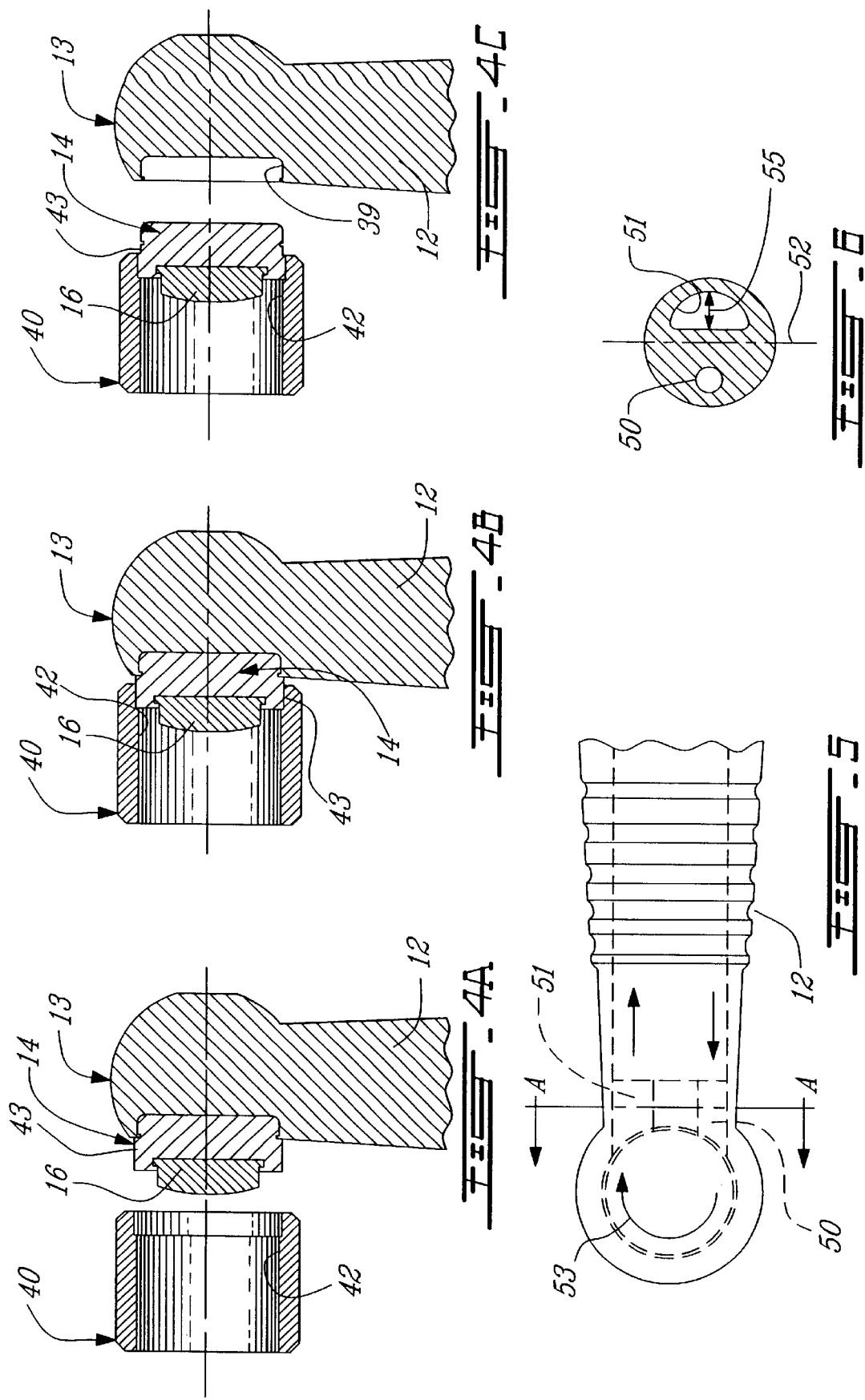

HIGH-SPEED DENTAL DRILL

FIELD OF THE INVENTION

The present invention relates to a high-speed miniature drill such as a dental drill having an improved cover design for accessing the turbine chamber, an improved air return port within the chamber and an overall exterior form which facilitates cleaning and sterilization of the dental drill handpiece.

BACKGROUND OF THE INVENTION

Most air-driven, high-speed dental handpieces provide a means of accessing the turbine assembly for maintenance purposes. The turbine assembly is located in a chamber formed in the head of the drill and includes chuck, bearings and impeller. The turbine assembly has a much shorter service life than the handpiece body and must be replaced periodically. Routine cleaning and lubrication may also necessitate accessing the turbine assembly periodically. Typically, a removable threaded insert is provided for the purpose of removing or servicing the turbine assembly. This threaded insert frequently incorporates a push button mechanism for disengaging the chuck and removing the cutting tool or burr. Removal of the threaded insert is generally facilitated by the use of a specially designed key or wrench which may be hexagonal or octagonal in shape and matches the exterior profile of the threaded inset. Other designs incorporate slots or flats in the threaded insert for receiving a corresponding key or wrench. Such prior art designs are exemplified, for example by reference to U.S. Pat. No. 5,334,013 issued on Aug. 12, 1994.

Air-driven, high-speed dental handpieces incorporate one or more air passages for supplying air to the turbine assembly and one or more exhaust passages for evacuating the return air from the turbine chamber. The effective area of the air exhaust passage is of great importance since a larger opening reduces the back pressure in the turbine chamber and increases the efficiency of the energy transfer by the air flow through the turbine and out through an exhaust passage produced in the chamber side wall. Air exhaust passages produced by conventional manufacturing processes such as drilling, produce holes with a circular cross-section which do not take full advantage of the available area within the handpiece head. Furthermore, the total available area for the air exhaust passage leading from the turbine chamber is limited by the fact that the handpiece head is generally designed to be as small as possible in order to improve accessibility and maneuverability within the confines of the patient's mouth. Certain handpiece designs incorporate multiple, circular air exhaust passages in order to increase the effective exhaust area.

SUMMARY OF THE INVENTION

It is a feature of the present invention to provide a high-speed dental drill which substantially overcomes the above-mentioned disadvantages of the prior art.

It is a further feature of the present invention to provide a high-speed dental drill having an improved insert for providing access to the turbine assembly and wherein the insert has a smooth conical tapered circumferential external sidewall for frictional engagement by a mating conical bore of a key for the removal and connection of the insert.

Another feature of the present invention is to provide a high-speed dental drill which has an exhaust port in the turbine assembly chamber which has a non-circular cross-section in which the aspect ratio of the exhaust port is not equal to one whereby to increase energy transfer to drive the turbine.

Another feature of the present invention is to provide a high-speed dental drill wherein the handpiece, the drill head and the insert are radially symmetric to facilitate cleaning and sterilization.

Another feature of the present invention is to provide a high-speed dental drill design which has no sharp corners, flats or slots on its exterior surfaces and wherein the manufacture of the drill is simplified.

According to the above features, from a broad aspect, the present invention provides a high-speed dental drill which comprises a handpiece having a drill head at an end thereof. The drill head has a turbine assembly supported in a turbine chamber inside the drill head. The turbine assembly has a chuck rotatably secured between bearings. An impeller is secured about the chuck and aligned with an air inlet port in a sidewall of a turbine chamber. An exhaust port is also provided in the sidewall. Conduit means are provided in the handpiece to direct air pressure to the air inlet port to drive the turbine and rotate the chuck. The chuck has a work bit engaging free end which is exteriorly accessible. An insert is removably secured to the drill head and provides access to the turbine chamber. The insert has a smooth conical tapered circumferential external sidewall for frictional engagement by a mating connecting bore of a key for the removal and connection of the insert.

According to a further broad aspect of the present invention there is provided a high-speed dental drill wherein the turbine is driven by air under pressure being fed to the turbine chamber to rotate the turbine and wherein the air is exhausted from the chamber through an exhaust port formed in a sidewall of a chamber and having a non-circular cross-section in which the aspect ratio of the exhaust port is not equal to one thereby increasing the energy transfer to drive the turbine.

According to a still further broad aspect of the present invention there is provided a high-speed dental drill and wherein the handpiece, the drill head and the insert are all radially symmetric to facilitate cleaning and sterilization as well as manufacturing.

BRIEF DESCRIPTION OF THE DRAWINGS

A preferred embodiment of the present invention will now be described with reference to the accompanying drawings in which

FIGS. 4A to 4C are section views showing how the key is engaged with the conical insert to remove the insert;

FIG. 5 is a top section view of the neck portion of the handpiece showing the position of the air inlet and air exhaust ports with respect to the turbine chamber; and FIG. 6 is a section view of the turbine chamber sidewall containing the air inlet and outlet ports.

DESCRIPTION OF PREFERRED EMBODIMENTS

Figure 1:
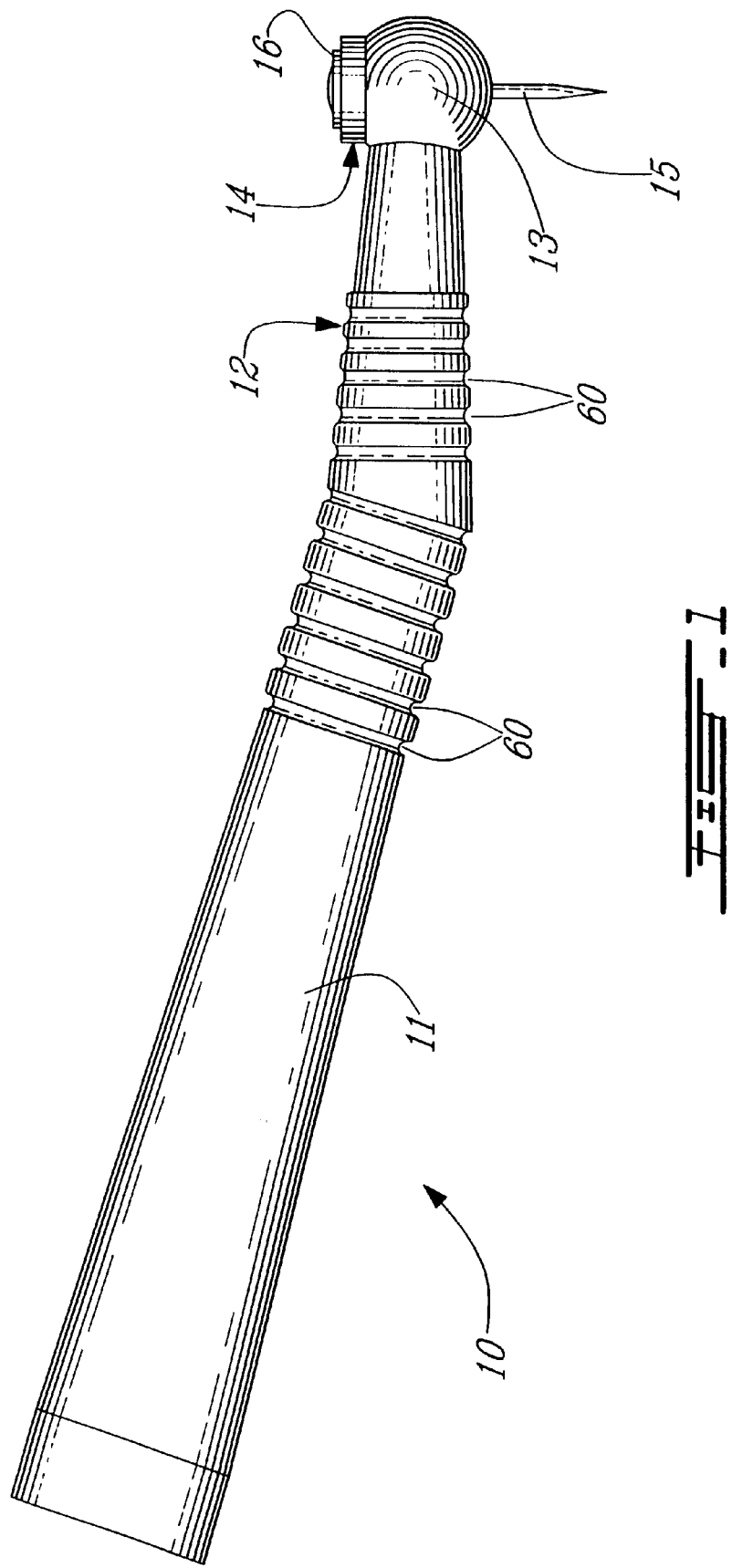
FIG. 1 is a perspective view of the high-speed dental drill of the present invention.

Referring now to the drawing and more particularly to FIG. 1 there is shown generally at 10 the high-speed dental drill of the present invention. The drill consists essentially of a handpiece 11 having an angulated neck section 12 and a spherical drill head 13 at the end of the neck section 12. An insert 14 is threadably secured to the drill head 13 to provide access to the inner turbine chamber, as will be described later. A cutting tool or burr 15 is secured to a chuck, as will be described later, and is rotatably driven by the turbine inside the drill head. The insert 14 is provided with a spring loaded button 16 provided with a smooth outer surface for the removal of the chuck.

Figure 2:
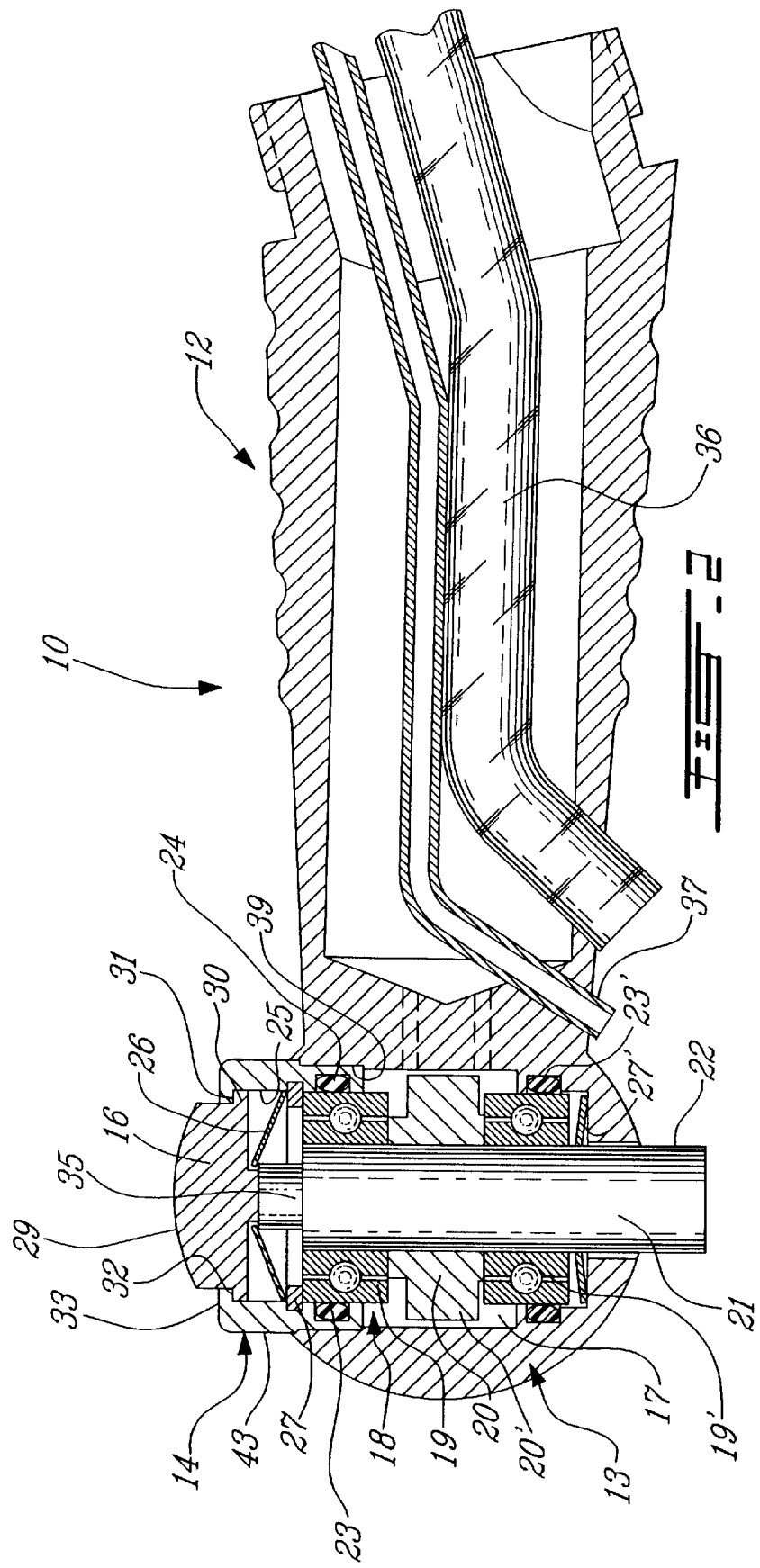
FIG. 2 is a longitudinal section view through the dental drill of the present invention.

Referring now to FIG. 2 there is shown a cross-sectional view of the high-speed dental drill of the present invention and as can be seen the spherical drill head 13 has a turbine chamber 17 formed therein for housing the turbine assembly 18. Essentially, the turbine assembly consists of a pair of bearings 19 and 19' which are spaced apart and disposed on opposed sides of an impeller 20 which is frictionally engaged to a chuck 21 whereby to rotate the chuck. The chuck has a work bit engaging free end 22 to which a drill bit or burr is connected.

As herein shown the bearings 19 and 19' are held in position between a retaining ring 27 and a spring washer 27'. O-rings 23 and 23' provide a compliant support for the bearings. The O-ring 23' is located within the spherical head housing while the O-ring 23 is held in a circular groove 24 formed in the inner sidewall 25 of the insert 14. A spring washer 26 is held in place by a retaining ring 27 held in a circular groove formed in the inner sidewall 25 of the insert whereby to bias the button 16 outwardly. The push button 16 has a spherical outer surface 29 and a circumferential flange 30 which is received under a shoulder portion 31 of a circular bore 32 formed in the top wall 33 of the cover 14. By depressing the button 16 against the action of the spring 26 the chuck 21 can be disengaged thereby allowing the removal of the drill or burr 15.

As herein shown a fiber optic bundle 36 extends within the handpiece and out of the forward section of the angulated neck portion 12 to direct a light beam in the area of the drill bit. A water nozzle 37 also exits adjacent the optic fiber to provide a jet of cool water in the area of the drill bit to cool the drill bit during its high-speed drilling operation.

Figure 3:
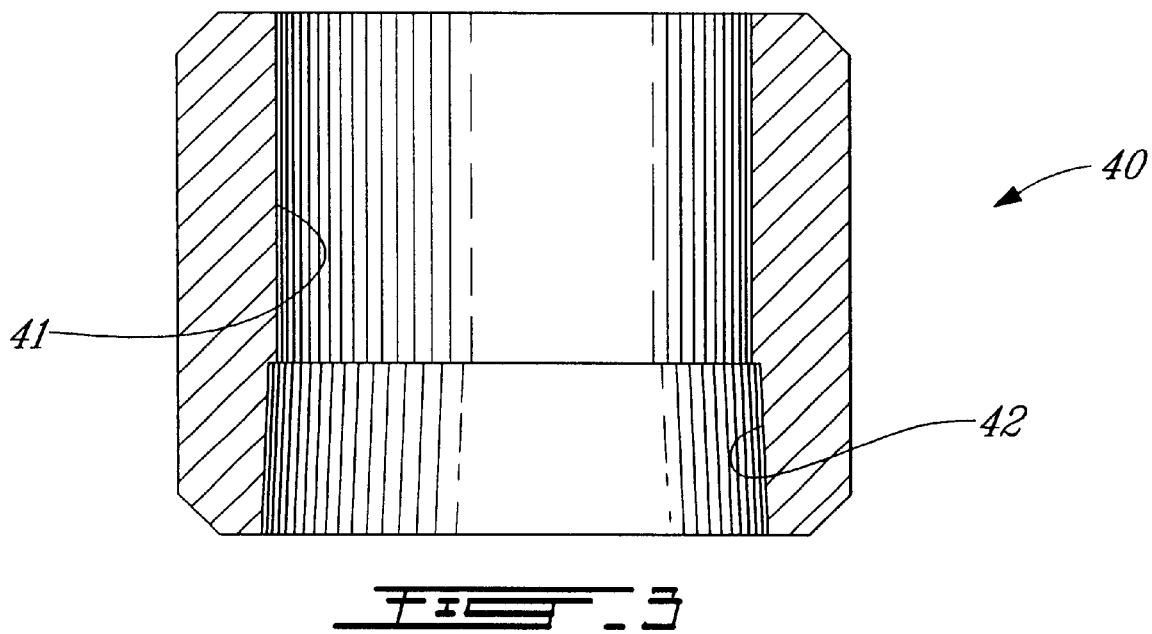
FIG. 3 is a section view illustrating the construction of the key for the connection and disconnection of the conical insert.

FIG. 3 illustrates the construction of a key 40 which is utilized to remove the insert 14 from threaded engagement within the threaded section 39 of the turbine housing or chamber. This key is formed as a cylinder provided with a cylindrical inner surface 41 which at one end thereof is provided with a female tapered conical bore section 42 which is dimensioned to receive in close frictional fit therein the male conical outer sidewall surface 43 of the insert 14. This permits the insert 14 to be engaged and rotated to threadably disengage it from the turbine assembly chamber, as is illustrated in FIGS. 4A to 4C. Alternately the inner surface of the key can be conical over its entire length as shown in FIGS. 4A to 4C.

As shown in FIG. 4A the key 40 has its conical female section 42 positioned over the male conical sidewall surface 43 of the insert 14 and pushed there against for frictional engagement. The key 40 is then rotated anti-clockwise to unthread the insert 14 from the spherical head. While the insert is removed it is retained by friction fit within the key 40. This provides the advantage that the insert does not become lost. One can appreciate that the insert is small and can easily be lost. Accordingly, this interconnecting arrangement of the insert 14 with the key 40 provides this additional feature of the present invention.

Another important feature of the present invention is illustrated in FIGS. 5 and 6 wherein there will be described the construction of the air inlet port 50 and the air exhaust port 51. Air under pressure is supplied to the inlet port 50 which is disposed adjacent the turbine 20 to one side of the rotational axis 52 of the turbine (see FIG. 6). As shown in FIG. 5 the air being injected through the inlet port 50 impinges upon the turbine vanes 20' causing the turbine to rotate and accordingly the chuck secured thereto to rotate. The air stream is guided along the chamber sidewall in the direction of arrow 53 (see FIG. 5) and exits through the exhaust port 51. To maximize the effective area of the air exhaust port 51, the port has a non-circular cross-section and is produced by means of, but not limited to, an electron discharge machining process. The exhaust port cross-sectional area is at least twice the cross-sectional area of a circle formed about the radius of said exhaust port. The radius is illustrated by reference numeral 55 in FIG. 6. While the non-circular cross-section opening of the exhaust port 51 is semi-circular in shape, it is possible that this shape can have other cross-sectional configurations which are not circular. However, it is important that the aspect ratio, that is to say the height divided by the width of the cross-sectional opening, is not necessarily equal to one whereby to maximize the effective area of the air exhaust passage. This causes the turbine to rotate at higher speeds due to improved air flow through the turbine chamber thereby increasing the energy transfer to drive the turbine 20.

As previously described the handpiece 11, the angular neck section 12 and the spherical head at 13 are radially symmetric and this allows them to be manufactured simply and economically out of stainless steel by means of a turning operation on a lathe. A portion of the handpiece and the angular neck section incorporate a series of circular grooves 60 for improved grip but these grooves are smooth in cross-section to prevent the accumulation of dirt or debris and the associated bacteria or viruses. Similarly, the insert is formed with smooth surfaces free of small crevices or corners which can potentially accumulate such debris which carry or form bacteria. The overall exterior form of the drill facilitates cleaning and sterilization of the device as well as manufacturing.

In conclusion, the high-speed dental drill as above described incorporates several features which can be summarized as follows. On the outer surface of the handpiece its neck section, the spherical head and cover, there are no sharp corners, flats or slots and this greatly facilitates cleaning and sterilization as well as manufacturing. In other words, there are no small crevices or corners which can potentially accumulate dirt or debris or, more importantly, the associated bacteria or viruses. Further, conical insert is removed by a novel key by frictional engagement and wherein the insert remains engaged in the key to prevent loss of the insert. Because the insert is radially symmetric, it can be manufactured simply and economically by means of a turning operation on a lathe. The key is easy to disconnect from the insert by applying a lateral force after the insert is threaded back onto the threaded opening in the head leading to the turbine chamber. By applying a slight lateral force the cones are easily disengaged. Furthermore, the effective area of the air exhaust passage for a given handpiece head size is greatly improved as it is not circular and maximizes the effective area of the air exhaust passage. The exhaust passage can also be produced by an electron discharge machining process. The handpiece and the head can also be produced by means of a turning operation on a lathe.

It is within the ambit of the present invention to cover any obvious modifications of the preferred embodiment described herein, provided such modifications fall within the scope of the appended claims.

What is claimed is:

1. A high-speed drill comprising a handpiece having a drill head at an end thereof, said drill head having a turbine assembly supported in a turbine chamber inside said drill head, said turbine assembly having a chuck rotatably secured between bearings, an impeller secured about said chuck and aligned with an air inlet port in a sidewall of said turbine chamber, an exhaust port in said sidewall, conduit means in said handpiece to direct air pressure to said air inlet port to drive said turbine and rotate said chuck, said chuck having a work bit engaging free end which is exteriorly accessible, an insert removably secured to said drill head and providing access to said turbine chamber, said insert having a smooth conical tapered circumferential external sidewall adapted for frictional engagement by a mating conical bore of a conical key for the removal and connection of said insert, said insert being threadably engaged in an access opening of said turbine chamber to provide quick access for lubricating or changing parts inside said spherical drill head.

2. A high-speed drill as claimed in claim 1 wherein said drill is a dental drill.

3. A high-speed drill as claimed in claim 2 wherein said key has a finger engaging peripheral wall for imparting rotational displacement thereof to thread and unthread said insert in said access opening.

4. A high-speed drill as claimed in claim 3 wherein said conical key is a cylindrical external key having an inner cylindrical bore, at least an end portion of said bore constituting said mating conical bore for gripping said insert, said conical key having an outer wall provided with a non-slip surface for improved finger gripping and rotation of said key when engaged and gripped with said insert.

5. A high-speed drill as claimed in claim 2 wherein said insert has a smooth top wall surface.

6. A high-speed drill as claimed in claim 5 wherein said smooth top wall surface is a dome shape top surface of a push button which is spring biased outwardly in a circular bore formed in a top wall of said insert, said insert having an overall smooth outer surface free of sharp corners.

7. A high-speed drill as claimed in claim 1 wherein said handpiece, said drill head and said insert are all radially symmetric to facilitate cleaning and sterilization as well as manufacturing.

8. A high-speed drill comprising a handpiece having a drill head at an end thereof, said drill head having a turbine assembly supported in a turbine chamber inside said drill head, said turbine assembly having a chuck rotatably secured between bearings, an impeller secured about said chuck and aligned with an air inlet port in a sidewall of said turbine chamber, an exhaust port in said sidewall, conduit means in said handpiece to direct air pressure to said inlet port to drive said turbine and rotate said chuck, said chuck having a work bit engaging free end which is exteriorly accessible, an insert removably and threadably engaged in an access opening of said turbine chamber and providing quick access to said turbine chamber for lubricating or changing parts inside said drill head, said exhaust port having a non-circular cross-section in which the aspect ratio of said exhaust port is not necessarily equal to one whereby to increase energy transfer from air flowing from said inlet port to said exhaust port to drive said turbine and a conical key having a finger engaging peripheral wall for imparting rotational displacement thereof to thread and unthread said insert in said access opening.

9. A high-speed drill as claimed in claim 8 wherein said exhaust port is of semi-circular cross-section and defines a cross-sectional area which is at least twice the cross-sectional area of a circle formed about the radius of said semi-circular cross-section of said exhaust port.

10. A high-speed drill as claimed in claim 9 wherein said sidewall of said turbine chamber is a radially symmetric sidewall, said air inlet port being disposed on a first side of said turbine axis, said exhaust port being disposed on an opposite side of said turbine axis whereby to create a smooth efficient air flow about said turbine to impart rotation thereto.

\* \* \* \* \*